(12) United States Patent
Song

(10) Patent No.: US 8,158,754 B2
(45) Date of Patent: Apr. 17, 2012

(54) MULTIPLE MODIFIED DERIVATIVES OF GELATIN AND CROSSLINKED MATERIAL THEREOF

(75) Inventor: Chan Song, Shanghai (CN)

(73) Assignee: Bioregen Biomedical (Changzhou) Co., Ltd., Changzhou (CN)

( * ) Notice: Subject to any disclaimer, the term of this patent is extended or adjusted under 35 U.S.C. 154(b) by 239 days.

(21) Appl. No.: 12/522,476

(22) PCT Filed: Sep. 29, 2007

(86) PCT No.: PCT/CN2007/002863
§ 371 (c)(1),
(2), (4) Date: Jul. 8, 2009

(87) PCT Pub. No.: WO2008/083542
PCT Pub. Date: Jul. 17, 2008

(65) Prior Publication Data
US 2009/0306345 A1 Dec. 10, 2009

(30) Foreign Application Priority Data
Jan. 9, 2007 (CN) .......................... 2007 1 0036276

(51) Int. Cl.
*C09H 3/00* (2006.01)
*C07K 14/00* (2006.01)
(52) U.S. Cl. ....................................... 530/354; 530/350

(58) Field of Classification Search .................. 530/354, 530/350
See application file for complete search history.

(56) References Cited

U.S. PATENT DOCUMENTS
2005/0176620 A1* 8/2005 Prestwich et al. ................ 514/2
* cited by examiner

*Primary Examiner* — Chih-Min Kam
(74) *Attorney, Agent, or Firm* — Birch, Stewart, Kolasch & Birch, LLP

(57) ABSTRACT

Disclosed is a kind of multiple modified derivatives of gelatin having not only the structure of formula (I) but also one of structures of formula (II), (III), and (IV) as well, wherein, G refers to gelatin residue, which can be type A, type B or a gelatin obtained from gene recombination; $R_1$ refers to alkylene, or a linkage group with amide; $R_2$ refers to alkyl, or aryl; $R_3$ refers to alkylene; and $R_4$ refers to carboxyl or carboxylate. The multiple modifying ways of gelatin comprise the hydrophobic modification on the amino group of gelatin through amide bond, carboxylation on the amino group of gelatin through amide bond, thiolation on the carboxyl group of gelatin, and thiolation following carboxylation on amino group of gelatin through amide bond. Also disclosed is a crosslinked material made of multiple modified derivatives of gelatin. The multiple modified derivatives of gelatin have flexible chemical structures and many properties. Their crosslinked gelatin material can be used the matrix for cell growth, etc.

17 Claims, 1 Drawing Sheet

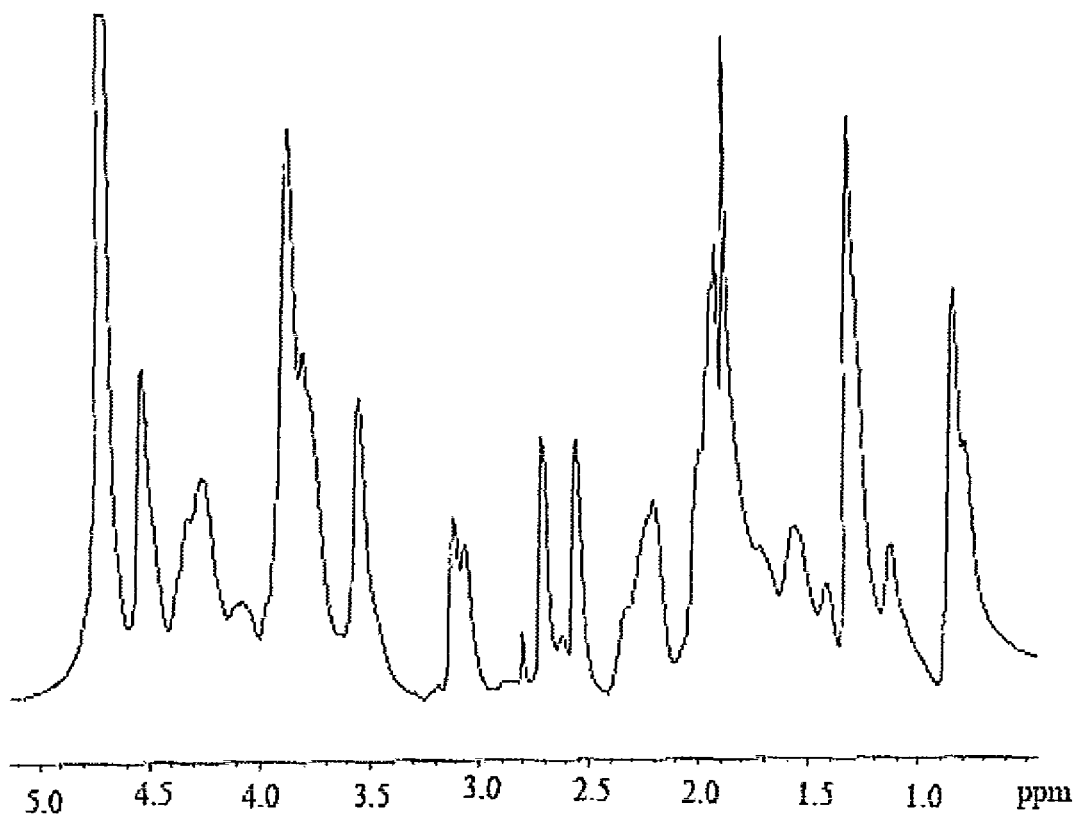

MULTIPLE MODIFIED DERIVATIVES OF GELATIN AND CROSSLINKED MATERIAL THEREOF

This application is the U.S. National Stage of International Application No. PCT/CN2007/002863, filed Sep. 29, 2007, which also claims the benefit of priority of Chinese Application No. 200710036276.5, filed Jan. 9, 2007. The entire contents of all are hereby incorporated by reference.

TECHNICAL FIELD

This invention relates to compound gelatin, especially to multiple modified derivatives of gelatin. In addition, it also relates to the crosslinked material that made from the derivatives.

BACKGROUND TECHNOLOGY

Gelatin is the denatured derivative of collagen, a protein containing 18 kinds of amino acids necessary for human body. Natural gelatin is usually prepared by acidic or alkalic hydrolysis of collagen in connective tissues e.g. animal skin, bone, sinew and ligament etc., separation and then extraction. Usually it can be divided A and B two types: the one prepared through acidic hydrolysis, with less side chain carboxylic acid residual group and higher isoelectric point, is called as A type; the one prepared through alkali hydrolysis is called as B type, with most glutamine and asparagine residue in side chains being transformed into glutamic acid and aspartic acid, therefore the side chains have more carboxylic acid residual group and it has lower isoelectric point. Natural gelatin, whether prepared by acidic method or alkalic method, is usually a complicated mixture, with many polypeptide of different molecular weight. Its property differs to some extent according to different batches. Gelatin can also be prepared through genetic recombination engineering, and the gelatin by this method has precise molecular weight, isoelectric point, and molecular structure which can be designed according to specific application (Olsen et al, Advanced Drug Delivery Reviews, 55, 1547, 2003).

Gelatin has many excellent properties such as biocompatibility, biodegradation and low immunogenicity etc. Therefore, it has wide usages in bio-medicine fields such as gelatin hemostasis sponge, gelatin capsule for drug, gelatin sponge wound dressing and new drug release formulation and tissue regeneration matrix etc. However, gelatin can dissolve into water at body temperature; therefore for the most applications of gelatin in bio-medicine, physical crosslinking and chemical crosslinking of gelatin to improve its thermal and mechanical stability is necessary. Dehydrogenation heat treatment and UV radiation are common methods for physical crosslinking, but their crosslinking efficacy is low and also uncontrollable. Chemical crosslinking has relatively higher efficacy. The common chemical crosslinkers include formaldehyde, glutaric dialdehyde, polyfunctional group epoxy crosslinker, polyfunctional group isocyanate crosslinker, acid azid diazoimido compounds and carbodiimide etc. (Kuijpers et al, Journal of Biomaterials Science: Polymer Edition, 11, 225, 2000). However, these chemical crosslinkers usually have severe toxic side effects, and even trace residue of chemical crosslinker and crosslinking functional groups may lead to severe inflammation. Therefore, the application of gelatin in bio-medicine field is seriously restricted by the current available chemical crosslinking method.

Chemical modification of gelatin is one important way to improve the application of gelatin in bio-medicine field, which can not only offer gelatin some important physical and chemical properties, but also reduce or not use the chemical crosslinker with toxic side effect in making crosslinked gelatin materials. For example, Ma et al disclosed a hydrophobically poly-lactic acid modified gelatin derivative with amphipathic properties in Journal of Biomaterials Science: Polymer Edition, 13, 67, 2002; Van Den Bulcke et al disclosed methylacrylamide modified gelatin derivative in Biomacromolecules, 1, 31, 2000, and this derivative can be used to prepare crosslinked gelatin material by free radical polymerization through relatively mild light-induction; Morikawa and Matsuda et al disclosed a N-isopropylacrylamide grafted gelatin derivative with temperature-responsive gelation property in Journal of Biomaterials Science: Polymer Edition, 13, 167, 2002; the thiolated gelatin derivative disclosed by Shu et al in Biomaterials, 24, 3825, 2003, can be used to prepare in situ crosslinked material through mild disulfide bond or nucleophilic addition method. So far, these methods still have many limits in preparing crosslinked gelatin material. Herein one important reason is the number of main functional groups of gelatin (amino group or carboxyl in side chain) available for chemical modification and crosslinking is considerably limited. For example, for type B gelatin, there is 28 side chain amino group and 118 side chain carboxyl per 1000 amino acid residual groups. There are similar side chain amino group content in terms of type A gelatin and type B gelatin, however, the content of side chain carboxyl in type A gelatin (54/1000 amino acid residues) which is far less than that in type B gelatin. Therefore, it is necessary to further develop novel method of chemical modification and crosslinking to further expand many kinds of application potential of gelatin in bio-medicine field.

Invention Contents:

One of technical problems to be resolved in this invention is to provide a kind of novel multiple modified derivatives of gelatin.

The other technical problem to be resolved in this invention is to provide a kind of novel crosslinked material made of multiple modified derivatives of gelatin.

In this invention gelatin is taken as raw material, and the novel multiple modified derivatives of gelatin is prepared by conducting hydrophobic modification on the side chain amino group of gelatin through amide bond, carboxylation on side chain amino group through the amide bond and then thiolation of carboxyl. Compared with the single modified derivatives of gelatin, the multiple modified derivatives of gelatin of this invention have many excellent properties such as adjustable side chain molecular structure and chemical properties etc., and may have many important applications in bio-medicine field.

The multiple modified derivatives of gelatin of this invention has undermentioned general formula structure (I) and at least one of the general formula structure (II), (III), and (IV) at the same time.

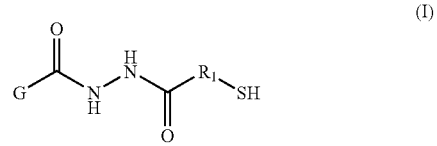

(I)

(II)

-continued

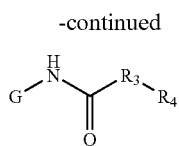
(III)

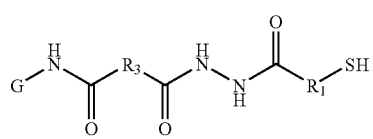
(IV)

Wherein G is a gelatin residue, including type A gelatin residue, type B gelatin residue, or a gelatin obtained from genetic recombination. $R_1$ is an alkylidene or a connection group with an amide bond. $R_2$ is an alkyl or an aryl. $R_3$ is alkylidene or a substituted alkylidene. R4 is carboxyl or carboxyl salt.

The above mentioned connection group containing one amide bond is

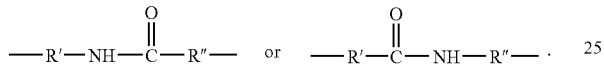

Wherein R' and R" are alkylidene group, substituted alkylidene, aryl or polyether group.

The above mentioned alkylidene group is —$(CH_2)_n$— (n is an integer from 1 to 15). Preferably n is an integer from 1 to 8

The above mentioned substituted alkylidene is an alkylidene group that one of its hydrogen atoms at least is substituted by alkyl, hydroxyl, amino, alkoxy, phenyl, ester group etc.

The above mentioned aryl is aromatic phenyl or naphthyl etc., and preferably phenyl.

The above mentioned polyether group is —$[(CHR)_nO]_m$, wherein R is an alkyl, n is an integer from 1 to 10, and m is an integer from 1 to 500. Preferably R is hydrogen atom, and n equal to 2, 3 and 4, respectively.

The above mentioned alkyl is a linear chain alkyl or a fork chain alkyl with 1~15 carbon atoms e.g. methyl, ethyl, propyl, isopropyl, butyl, isobutyl, tert-butyl, sec-butyl, amyl, neoamyl, hexyl, heptyl, octyl etc., and preferably linear chain or fork chain alkyl containing 1~10 carbon atoms, especially preferably methyl, ethyl, propyl, butyl, amyl, hexyl, heptyl and octyl.

The above mentioned alkoxyl is linear chain or fork chain alkoxyl containing 1~6 carbon atoms e.g. methoxyl, ethoxyl, propoxy, isopropoxy, butoxy, isobutoxy, tert-butoxy, sec-butoxy, pentyloxy, neo-pentyloxy and hexyloxy etc, and preferably linear chain or fork chain alkoxyl containing 1~4 carbon atoms, especially preferably methoxyl and ethoxyl.

The above mentioned ester group is —C(O)OR, wherein R is low alkyl group above mentioned, and preferably carbomethoxy, carbethoxy, propyl ester group and butyl ester group.

The above mentioned carboxyl is —COOH. Carboxyl salt is the group resulting from the above mentioned carboxyl neutralized by alkali i.e. —COO$^{31}$A$^+$, wherein A$^+$contains sodium, potassium ion, lithium ion and ammonium ion etc., and preferably carboxyl, carboxyl sodium salt or carboxyl potassium salt.

The multiple modified derivatives of gelatin of this invention has following several kinds of representative chemical structural general formulas:

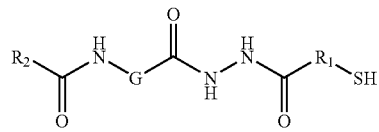
(V)

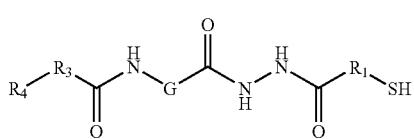
(VI)

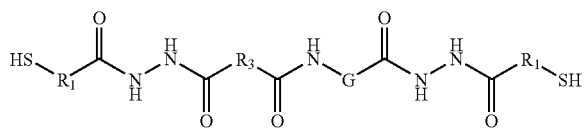
(VII)

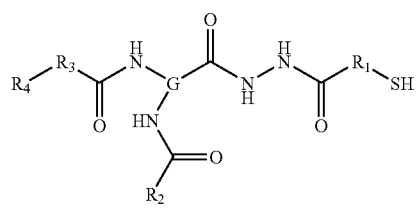
(VIII)

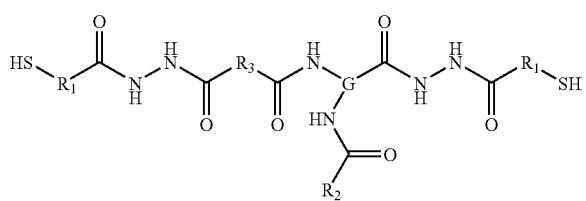
(IX)

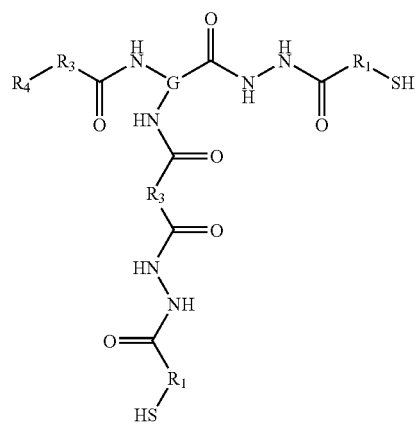
(X)

(XI)

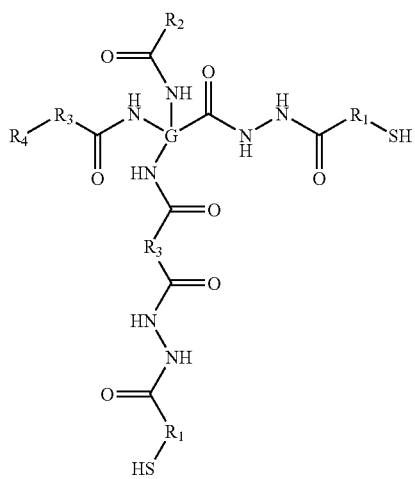

Wherein, the definition of G, $R_1$, $R_2$, $R_3$ and $R_4$ are the same as before.

The preferable chemical structures of $R_1$, $R_2$, $R_3$ and $R_4$ in the multiple modified derivatives of gelatin of this invention are as follows:

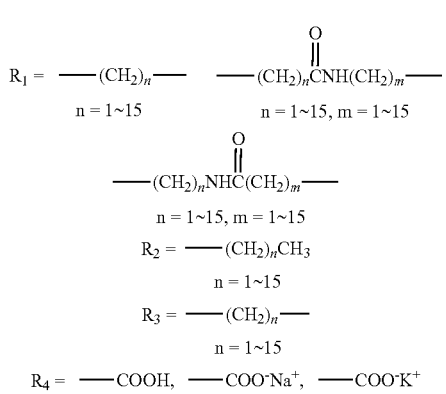

The multiple modified derivatives of gelatin in the above mentioned general formulas from (V) to (XI) all contain at least one thiol. General formulas (V), (VI), and (VII) are the chemical structure formula of double modified derivatives of gelatin of this invention. General formulas (VIII), (IX) and (X) are the chemical structure formula of triple modified derivatives of gelatin of this invention. General formula (XI) is the chemical structure formula of quadruple modified derivatives of gelatin of this invention.

The chemical modification of this invention on the multiple modified derivatives of gelatin contains the following four modes: (A) hydrophobic modification on the side chain amino group of gelatin through amide bond; (B) carboxylation on the side chain amino group of gelatin through amide bond; (C) thiolation on the side chain carboxyl of gelatin; (D) thiolation after carboxylation on the amino group of gelatin through amide bond.

For chemical modification mode (A), the commonly used method for hydrophobic modification on the side chain amino group of gelatin through amide bond is as follows:

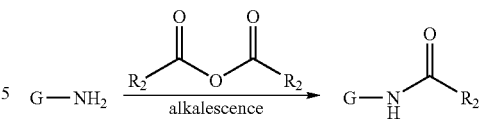

Wherein, the definition of G and $R_2$ are the same as previously. The detailed commonly used preparation process is to dissolve gelatin in warm water to make aqueous solution (usually at 30° C.), then adjust the pH value of solution to alkalescence (usually 8~10). After that, add in anhydride, stir to react for a certain time, and at the same time add in appropriate amount of aqueous alkali solution (e.g. sodium hydroxide) to maintain the reaction solution as alkalescence. Finally, dialyze and purify the reaction solution, freeze drying to get the product. The adopted anhydride contains acetic anhydride, propionic anhydride, butyric anhydride, valeric anhydride, caproic anhydride, heptanoic anhydride and octanoic anhydride etc.

For chemical modification mode (B), the commonly used method for carboxylation on the side chain of gelatin through amide bond is as follows:

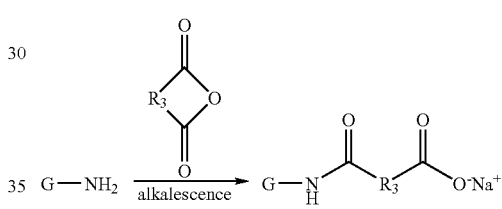

The detailed commonly used preparation process is to dissolve gelatin in warm water to make aqueous solution (usually at 30° C.), then adjust the pH value of solution to alkalescence (usually 8~10). After that, add in diacid anhydride, stir to react for a certain time, and at the same time add in appropriate amount of aqueous alkali solution (e.g. sodium hydroxide) to maintain the reaction solution as alkalescence. Finally, dialyze and purify the reaction solution, freeze drying to get the product. The adopted diacid anhydride contains butanedioic anhydride, glutaric anhydride, hexanedioic anhydride, maleic anhydride, heptanedioic anhydride, and octandioic anhydride etc.

For chemical modification mode (C) and (D), the chemical method of hydrazide/carbodiimide coupling (Shu et al, Biomacromolecules, 3, 1304, 2002) is adopted to conduct thiolation on the side chain carboxyl of gelatin (includes the introduced carboxyl from carboxylation on the side chain amino group of gelatin through amide bond). Its fundamental principle is that, the side chain carboxyl of gelatin (or the introduced carboxyl from carboxylation on the side chain amino group of gelatin through amide bond) produces reactive intermediate under the activation of carbodiimide, then the hydrazide amino of dithio-dihydrazide react with the reactive intermediate by nucleophilic attack to produce affixture, finally the disulfide bond of the affixture is reduced into free thiol, and then the product is collected after purification. Wherein the commonly used method is as follows:

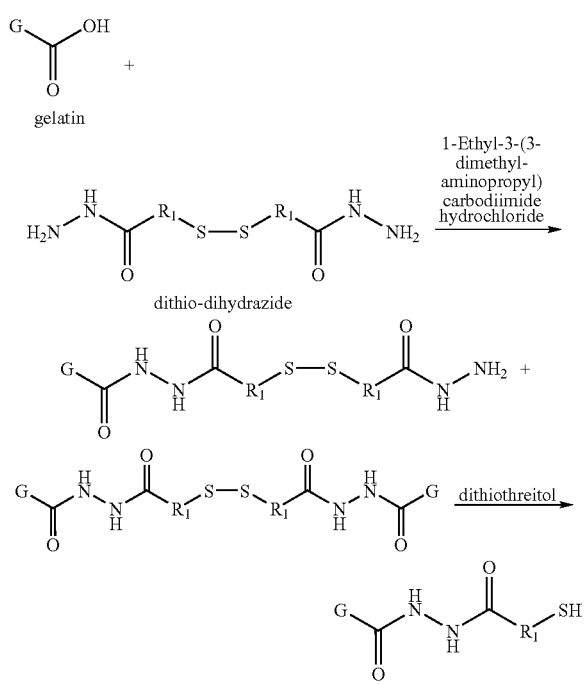

Wherein, the definitions of G and R1 are the same as previously. The detailed commonly used preparation process is to dissolve gelatin or the carboxylation modified derivatives of gelatin into warm water to make aqueous solution (usually at 30° C.), then adjust the pH value of solution to subacidity (usually 4.75). After that, add into a certain dithio-dihydrazide, stir and dissolve it, then add a certain amount of 1-ethyl-3-(3-dimethylamino propyl)carbodiimide hydrochloride, and at the same time add into appropriate amount of acid solution continuously (e.g. hydrochloric acid) to maintain the pH value of reaction solution at 4.75; Finally under the condition of alkalescence (usually the pH value is 8~10), add into reducer such as hydroxy thiol, dithiothreitol or sodium borohydride etc. to reduce the disulfide bond into free thiol, the impurities are removed by dialysis and purification under acid condition, and freeze drying to get the product.

With regard to chemical modification way (C) and (D), for the thiolation on the side chain carboxyl of gelatin (or the introduced carboxyl from carboxylation on the side chain amino group of gelatin through amide bond), the commonly adopted representative dithio-dihydrazides include dithiodipropionic dihydrazide (DTPDH) and dithiodibutanoic dihydrazide (DTBDH) published in Biomacromolecules, 3, 1304, 2002 by Shu et al., and the new dihydrazide compounds published in invention patent application by us (Chinese patent application number: 200610118715.2; invention name: dihydrazide compounds and preparation method and usage thereof), including dithiodipropionic diacyl glycine dihydrazide (abbr. DGDTPDH), dithiodipropionic diacyl alanine dihydrazide (abbr. DADTPDH), dithiodipropionic diacyl(hydroxyl)aminoacetic dihydrazide (abbr. DHADTPDH), dithiodipropionic diacyl aminopropionic dihydrazide (abbr. DPDTPDH), dithiodipropionic diacyl aminobutyric dihydrazide (abbr. DBDTPDH), di-dipropionic diacyl cystamino dihydrazide (abbr. DPCDH), disuccinic diacyl cystamino dihydrazide (abbr. DSCDH), di(methyl)-succinic diacyl cystamino dihydrazide (abbr. DMPCDH), diglutaric diacyl cystamino dihydrazide (abbr. DGCDH), and diadipic diacyl cystamino dihydrazide (abbr. DACDH) etc. The chemical structural formula of these representative dithio-dihydrazides are as follows:

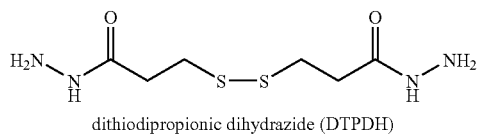
dithiodipropionic dihydrazide (DTPDH)

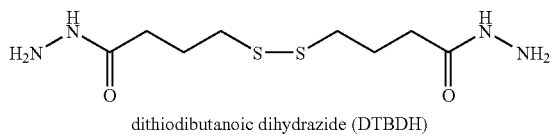
dithiodibutanoic dihydrazide (DTBDH)

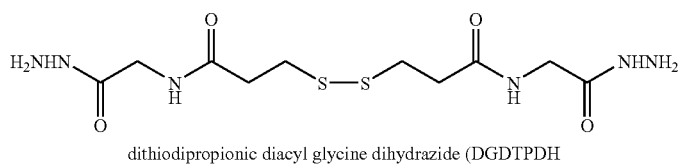
dithiodipropionic diacyl glycine dihydrazide (DGDTPDH)

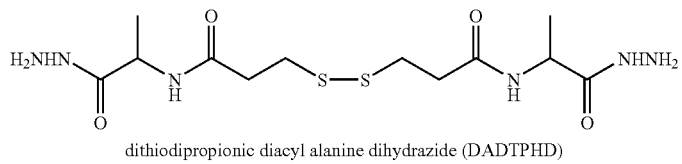
dithiodipropionic diacyl alanine dihydrazide (DADTPHD)

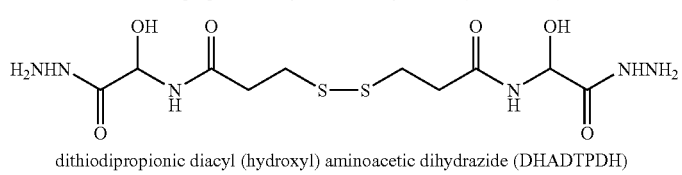
dithiodipropionic diacyl (hydroxyl) aminoacetic dihydrazide (DHADTPDH)

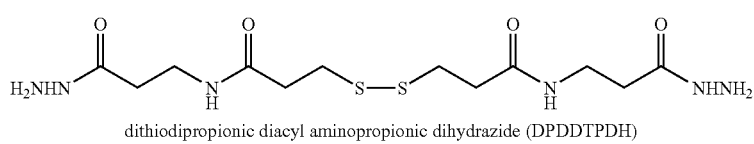
dithiodipropionic diacyl aminopropionic dihydrazide (DPDDTPDH)

-continued

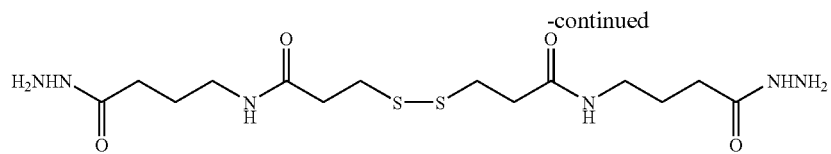
dithiodipropionic diacyl aminobutyric dihydrazide (DBDTPDH)

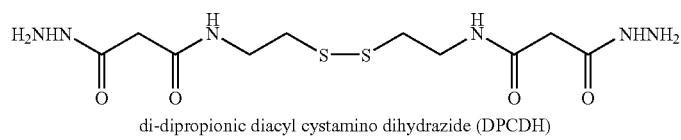
di-dipropionic diacyl cystamino dihydrazide (DPCDH)

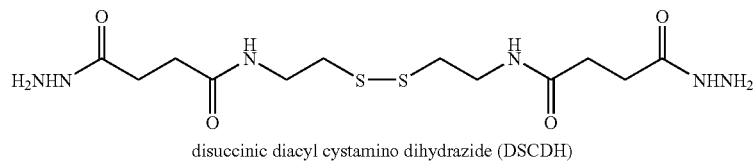
disuccinic diacyl cystamino dihydrazide (DSCDH)

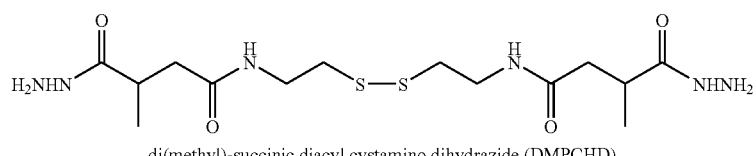
di(methyl)-succinic diacyl cystamino dihydrazide (DMPCHD)

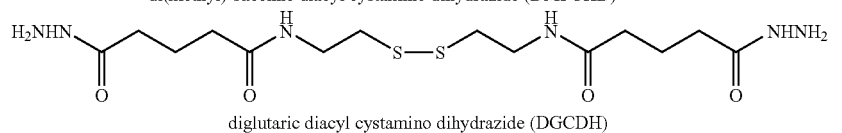
diglutaric diacyl cystamino dihydrazide (DGCDH)

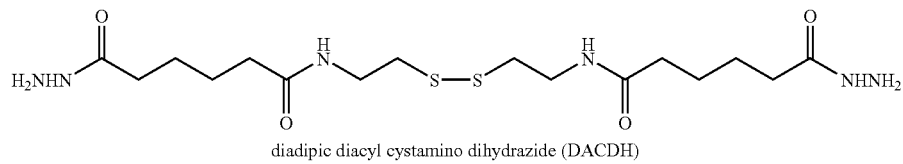
diadipic diacyl cystamino dihydrazide (DACDH)

The preparation of multiple modified derivatives of gelatin represented by above mentioned general formula (V) includes two processes: chemical modification mode (A) i.e. hydrophobic modification on the side chain amino groups of gelatin through amide bond, and chemical modification mode (C) i.e. thiolation on the side chain carboxyl of gelatin. The commonly adopted preparation method is divided into two steps: (1) to dissolve gelatin in warm water to make aqueous solution (usually at 30° C.), then adjust the pH value of solution to alkalescence (usually 8~10). After that, add in anhydride, stir to react for a certain time, and at the same time add in appropriate amount of aqueous alkali (e.g. sodium hydroxide) to maintain the reaction solution as alkalescence. Finally, dialyze and purify the reaction solution, freeze drying to get the intermediate; (2) to dissolve the intermediate in warm water to make aqueous solution or to use the above unpurified intermediate solution directly (usually at 30° C.), then adjust the pH value of solution to subacidity (usually 4.75). After that, add in a certain amount of dithio-dihydrazide, stir and dissolve it, and then add a certain amount of 1-ethyl-3-(3-dimethylamino propyl) carbodiimide hydrochloride, and at the same time add into appropriate amount of acid solution continuously (e.g. hydrochloric acid) to maintain the pH value of reaction solution at 4.75; Finally under the condition of alkalescence (usually the pH value is 8~10), add in reducing agents such as hydroxyl thiol, dithiothreitol or sodium borohydride etc. to reduce the disulfide bond into free thiol, the impurities are purified by dialysis under acid condition. Freeze drying to get the multiple modified derivatives of gelatin represented by general formula (V) of this invention. The adopted acid anhydride include acetic anhydride, propionic anhydride, butyric anhydride, pentanoic anhydride, hexanoic anhydride, heptanedioic anhydride, and octandioic anhydride etc., and the adopted dithio-dihydrazides refer to those above mentioned.

The preparation of multiple modified derivatives of gelatin represented by above mentioned general formula (VI) includes two processes: chemical modification mode (B) i.e. carboxylation on the side chain amino group of gelatin through amide bond, and chemical modification mode (C) i.e. thiolation on the side chain carboxyl of gelatin. The commonly adopted preparation method is divided into two steps: (1) to dissolve gelatin in warm water to make aqueous solution (usually at 30° C.), then adjust the pH value of solution to subacidity (usually 4.75). After that, add in a certain amount of dithio-dihydrazide, stir and dissolve, then add in a certain amount of 1-ethyl-3-(3-dimethylamino propyl) carbodiimide hydrochloride, and at the same time add in appropriate amount of acid solution continuously (e.g. hydrochloric acid) to maintain the pH value of reaction solution at 4.75; Finally under the condition of alkalescence (usually the pH value is 8~10), add in reduce agents such as hydroxyy thiol, dithiothreitol or sodium borohydride etc. to reduce the disulfide bond into free thiol, the impurities are purified by dialysis under acid condition. Freeze drying to get the intermediate. (2) to dissolve the intermediate into warm water to make aqueous solution under the protection of inert gas (e.g. Nitrogen etc.) (usually at 30° C.), then adjust the pH value of solution to alkalescence (usually 8~10). After that, add in diacid anhydride, stir to react for a certain time, add in appropriate amount of aqueous alkali solution (e.g. sodium hydroxide) to maintain the reaction solution as alkalescence at the same time. Finally, purifying by dialyze the reaction solution under acid condition, and then freeze drying to get the multiple modified derivatives of gelatin represented by general formula (VI) of this invention. The adopted diacid anhydride includes butanedioic anhydride, glutaric anhydride, and hexanedioic anhydride etc., and the adopted dithio-dihydrazides refer to those above mentioned.

The preparation of multiple modified derivatives of gelatin represented by above mentioned general formula (VII) and (X) includes three processes: chemical modification mode (B) i.e. carboxylation on the side chain amino group of gelatin through amide bond, chemical modification mode (C) i.e. thiolation on the side chain carboxyl of gelatin, and chemical modification mode (D) i.e. thiolation after carboxylation on the amino group of gelatin through amide bond. The commonly adopted preparation method is divided into two steps: (1) to dissolve gelatin in warm water to make aqueous solution (usually at 30° C.), then adjust the pH value of solution to alkalescence (usually 8~10). After that, add in diacid anhydride, stir to react for a certain time, add in appropriate amount of aqueous alkali solution (e.g. sodium hydroxide) to maintain the reaction solution as alkalescence at the same time. Finally, dialyze and purify the reaction solution, and then freeze drying to get the intermediate. (2) to dissolve the intermediate into warm water to make aqueous solution or directly use the unpurified intermediate solution (usually at 30° C.), then adjust the pH value of solution to subacidity (usually 4.75). After that, add into a certain amount of dithio-dihydrazide, stir and dissolve, then add a certain amount of 1-ethyl-3-(3-dimethylamino propyl) carbodiimide hydrochloride, and at the same time add into appropriate amount of acid solution continuously (e.g. hydrochloric acid) to maintain the pH value of reaction solution at 4.75; Finally under the condition of alkalescence (usually the pH value is 8~10), add in reduce agents such as hydroxyy thiol, dithiothreitol or sodium borohydride etc. to reduce the disulfide bond into free thiol, the impurities are removed by dialysis and purification under acid condition. Freeze drying to get the product. If there is an overdose of 1-ethyl-3-(3-dimethylamino propyl) carbodiimide hydrochloride used in the reaction, then all carboxyls are modified into thiol, and the product is the multiple modified derivatives of gelatin represented by general formula (VII) of this invention; If there is less 1-ethyl-3-(3-dimethylamino propyl) carbodiimide hydrochloride used in the reaction, then only part of carboxyls are modified into thiol, and the product is the multiple modified derivatives of gelatin represented by general formula (X) of this invention. The adopted diacid anhydride includes butanedioic anhydride, glutaric anhydride, and hexanedioic anhydride etc., and the adopted dithio-dihydrazides refer to those above mentioned.

The preparation method for multiple modified derivatives of gelatin represented by above mentioned general formula (VIII) is substantially the same with that for multiple modified derivatives of gelatin represented by above mentioned general formula (VI), as long as adding anhydride and diacid anhydride simultaneously in the step (2) for preparation of multiple modified derivatives of gelatin represented by above mentioned general formula (VI).

The preparation method for multiple modified derivatives of gelatin represented by above mentioned general formulas (IX) and (XI) is substantially the same with that for multiple modified derivatives of gelatin represented by above mentioned general formulas (VII) and (X), as long as adding anhydride and diacid anhydride simultaneously into the step (2) for preparation of multiple modified derivatives of gelatin represented by above mentioned general formulas (VII) and (X). If there is an overdose of 1-ethyl-3-(3-dimethylamino propyl)carbodiimide hydrochloride used in the reaction, then all carboxyls are modified into thiols, and the product is the multiple modified derivatives of gelatin represented by general formula (IX) of this invention; if there is less 1-ethyl-3-(3-dimethylamino propyl)carbodiimide hydrochloride used in the reaction, then only part of carboxyls are modified into thiol, and the product is the multiple modified derivatives of gelatin represented by general formula (XI) of this invention.

The novel multiple modified derivatives of gelatin of this invention has at least one side chain free thiol, which can be re-oxidized to form disulfide bond under certain conditions. Moderate oxidants such as oxygen, low concentration of peroxide, iodine, trivalent iron ion etc., all can transform the free thiol into disulfide bond, thereby prepare crosslinked gelatin material. Its general preparation method is that the aqueous solution of multiple modified derivatives of gelatin of this invention is oxidized into disulfide bond crosslinked material using air under neutral or alkalescence conditions; or oxidized into disulfide bond crosslinked material using low concentration of stronger oxidants such as hydrogen peroxide or trivalent iron ion etc under weak acid or acid conditions.

The crosslinked material of multiple modified derivatives of gelatin of this invention can also be prepared through cross-linking between multiple modified derivatives of gelatin of this invention and thiol-reactive crosslinker. The thiol-reactive functional group adopted in this invention includes maleimide, vinyl sulfone, α,β-unsaturated acrylic ester, α,β-unsaturated methyl acrylic ester, halo-propionic ester, halo-propionamide, disulfo-pyridine, N-hydroxyl succimide activated ester etc. Wherein, maleimide, vinyl sulfone, iodo-propionic ester, iodo-propionamide, disulfo-pyridine etc functional groups have high thiol-reactivity. These reactions can be divided into three classes: (1) the addition reaction between thiol and active unsaturated double bond, wherein the functional groups belonging to this reaction contain maleimide, vinyl sulfone, α,β-unsaturated acrylic ester, α,β-unsaturated methyl acrylic ester etc. (2) The substitution reaction between thiol and active alkylogen, wherein the functional groups belonging to this reaction contain iodo-propionic ester, bromo-propionic ester, chloro-propionic ester, iodo-propionamide, iodo-propionamide, chloro-propionamide, and disulfo-pyridine etc. (3) the last class is thioesterification reaction, and the functional groups of this reaction contain activated esters of various carboxylic acids e.g. N-hydroxyl succimide activated ester etc. Take the multiple modified derivatives of gelatin represented by general formula (V) of this invention as an example, the reaction equations between sulfhydryl and these functional groups are as follows:

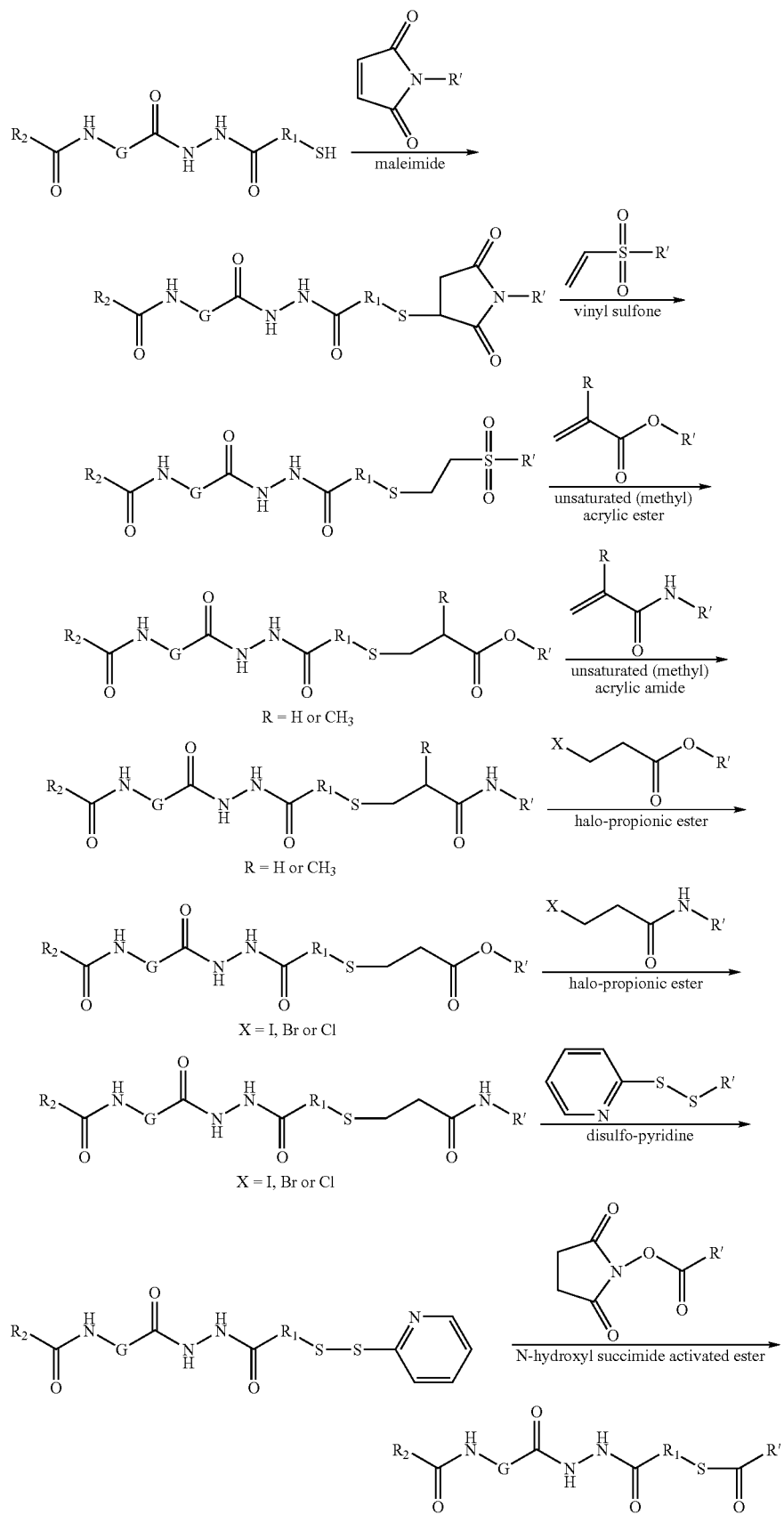

The thiol-reactive crosslinker adopted by this invention is polyethylene glycol (abbr. PEG) derivatives with at least two above mentioned functional groups e.g. two-arm, three-arm, four-arm, eight-arm or multiple-arm PEG derivatives, and they have the following typical chemical structures:

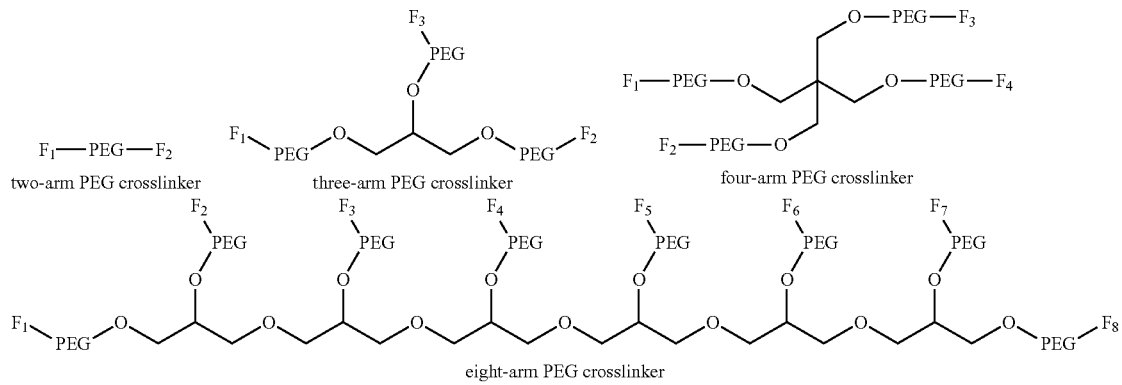

Wherein, $F_1$, $F_2$, $F_3$, $F_4$, $F_5$, $F_6$, $F_7$ and $F_8$ are above mentioned thiol-reactive functional groups e.g. maleimide, vinyl sulfone, α,β-unsaturated acrylic ester, α,β-unsaturated methyl acrylic ester, halo-propionic ester, halo-propanamide, disulfo-pyridine, N-hydroxyl succimide etc., and they may have totally or partially same, or totally different chemical structures. PEG refers to the segmer having repetitive units of $CH_2CH_2O$ whose molecular weight is from 100 to 1000000.

Take two-arm PEG as an example, the common crosslinker adopted by this invention contains PEG di-maleimide, PEG divinyl sulfone, PEG di-acrylic ester, PEG di-acrylamide, PEG di-halo-propionic ester, PEG di-halo-propanamide, PEG di-dithio-pyridine, and PEG di-N-hydroxyl succimide etc. There chemical structures are as follows:

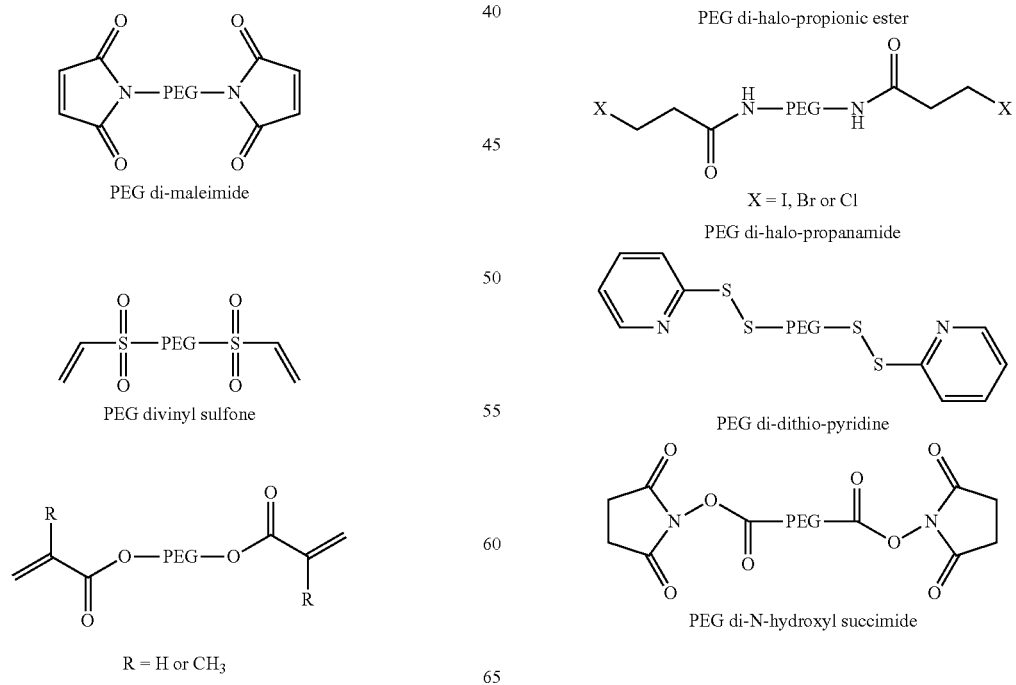

The general preparation method, adopted by this invention, for novel crosslinked material made of the multiple modified derivatives of gelatin crosslinked by thiol-reactive crosslinker is to make the multiple modified derivatives of gelatin of this invention into aqueous solution or mixed aqueous solution, adjust the pH value of solution to be neutral, then add in above above mentioned two-arm PEG derivative crosslinker and the multiple modified derivatives of gelatin represented by general formula (V) of this invention as an example, the prepared crosslinking material has the following chemical structure:

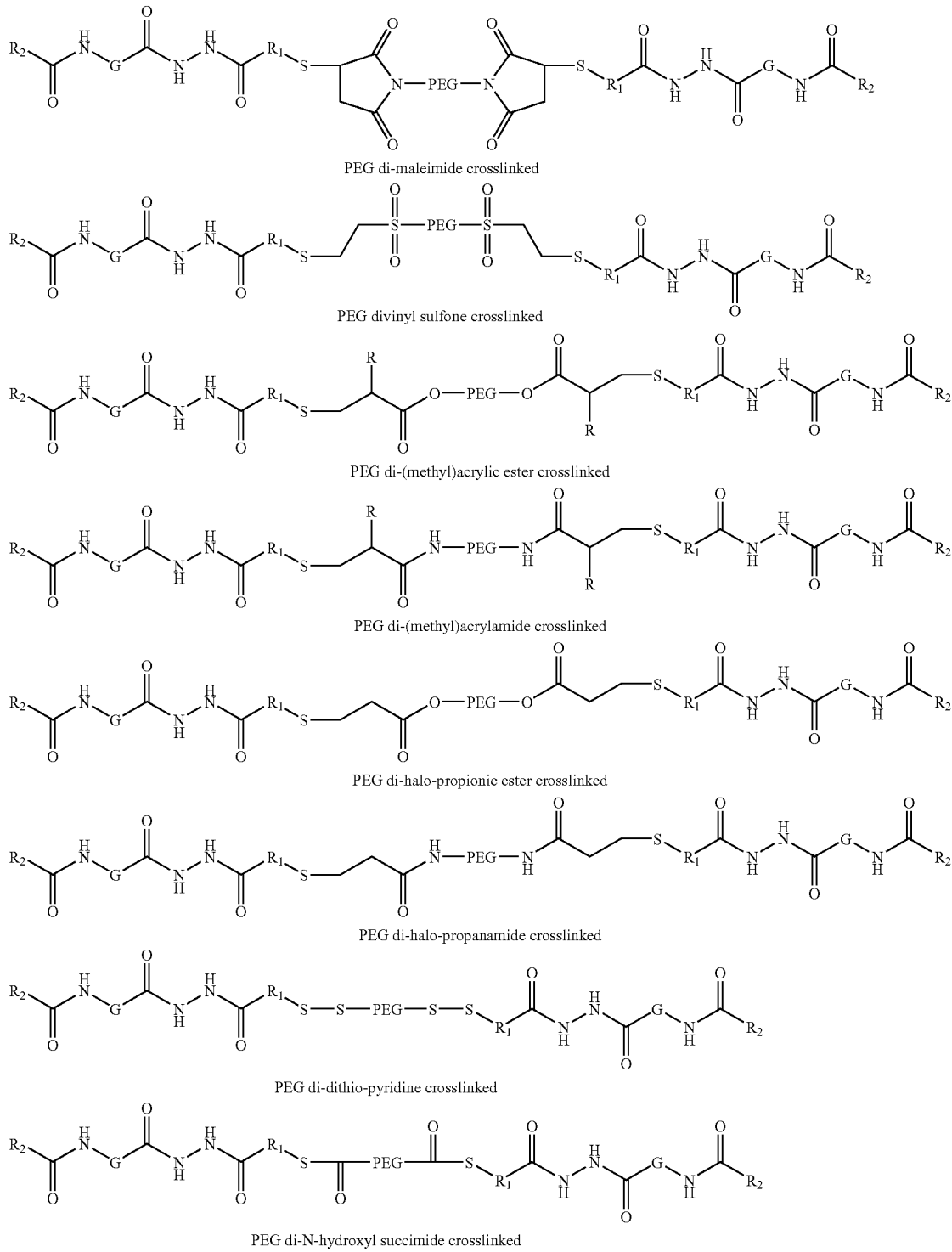

mentioned thiol-reactive crosslinker aqueous solution, after mixed uniformly, keep standing at room temperature for a moment and then get the gel i.e. crosslinked material. Take Similar to the multiple modified derivatives of gelatin represented by general formula (V) of this invention, the multiple modified derivatives of gelatin represented by general formula (VI), (VII), (VIII), (IX), (X) and (XI) of this invention also contain at least one thiol, and the same above mentioned crosslinking mode can also be used to prepare crosslinked material. In addition, co-crosslinking with a multi-arm PEG derivative crosslinker can also be adopted to prepare the crosslinked material made of multiple modified derivatives of gelatin of this invention. In addition, two or more above PEG derivative crosslinkers (e.g. two-arm PEG derivatives, three-arm PEG derivative cross-linker, four-arm PEG derivative crosslinker, eight-arm PEG derivative cross-linker etc.) can be adopted to prepare cross-linked material made of multiple modified derivatives of gelatin of this invention. The above mentioned preparation method, in combination with two or more above multiple modified derivatives of gelatin of this invention simultaneously, can be used to prepare the crosslinked material of gelatin.

DRAWING DESCRIPTION

FIG. 1 shows the HNMR spectrum and assignments of important chemical shift peaks of acetylated and thiolated multiple modified derivatives of gelatin in example 1. (with $D_2O$ as the solvent).

THE BEST WAY TO IMPLEMENT THIS INVENTION

The following examples may allow the technicians in this field more comprehensively understand the invention instead of restricting it in any mode.

EXAMPLE 1

Synthesis and Characterization of Acetylated and Thiolated Multiple Modified Derivatives of Gelatin (the Multiple Modified Derivatives of Gelatin Represented by General Formula (V) of this Invention, wherein, $R_1$=—$CH_2CH_2$—, $R_2$=—$CH_3$)

(1) Acetylation of Gelatin
Dissolve 1 g gelatin (type B, made from cowskin, Sigma, America) in 100 ml distilled water (about 30° C.), and get the clear and transparent solution. Use 1.0 mol/l sodium hydroxide solution to adjust the solution pH to about 9.5, then add in 0.05 g acetic anhydride (analytical pure) under magnetic stirring, add in appropriate amount of 1.0 mol/l sodium hydroxide solution continuously to maintain the solution pH at alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (acetylated gelatin) about 0.8 g.

(2) Thiolation of Acetylated Gelatin
Take above mentioned acetylated gelatin 0.5 g to dissolve in 50 ml distilled water (about 30° C.). Add 0.3 g dithiodipropionic dihydrazide in the above mentioned solution (prepared according to the method published by Shu et al in Biomacromolecules, 3, 1304, 2002), stir and dissolve. Then use 0.1 mol/l hydrochloric acid to adjust the pH value of solution to 4.75, add in 0.25 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the solution pH at 4.75. After reaction under magnetic stirring for 2 hours, add in 2.5 g dithiothreitol (Diagnostic Chemical Limited, America) and 0.1 mol/l sodium hydroxide solution, stir, and adjust the solution pH to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.35 g.

(3) The Characterization of Acetylated and Thiolated Multiple Modified Derivatives of Gelatin
The chemical structure of acetylated and thiolated multiple modified derivatives of gelatin is as follows:

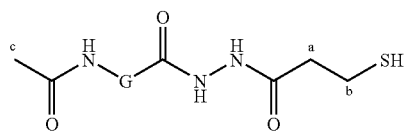

No small molecule impurity eluting peak is detected using GPC (with pure water as mobile phase, absorption detection being conducted at ultraviolet 210 nm), which indicates that the acetylated and thiolated multiple modified derivatives of gelatin is highly purified, and impurity is below the detection level of the instrument.

Using 2,4,6-trinitrobenzenesulfonic acid (TNBS) reagent, it is measured that 37% side chain amino groups of gelatin were acetylated.

Determination the active thiol content of acetylated and thiolated multiple modified derivatives of gelatin using improved method published by Shu et al in Biomacromolecules, 3, 1304, 2002, and the value is 0.5 mmol thiol/g.

Detection using $^1$H-NMR (with $D_2O$ as the solvent): refer to FIG. 1.

EXAMPLE 2

Synthesis and Characterization of Caproylated and Thiolated Multiple Modified Derivatives of Gelatin (the Multiple Modified Derivatives of Gelatin Represented by General Formula (V) of this Invention, wherein, $R_1$=—$CH_2CH_2$—, $R_2$=—$CH_2CH_2CH_2CH_2CH_3$)

(1) Caproylation of Gelatin
Dissolve 1 g gelatin (type A, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.1 g caproic anhydride (analytical pure) under magnetic stirring, add in appropriate amount of 1.0 mol/l sodium hydroxide solution continuously to maintain the pH value of solution as alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (caproylated gelatin) about 0.8 g.

(2) Thiolation of Caproylated Gelatin

Take above mentioned caproylated gelatin 0.5 g to dissolve in 50 ml distilled water (about 30° C.). Add 0.3 g dithiodipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.25 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the solution pH at 4.75. After reaction under magnetic stirring for 2 hours, add in 2.5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.37 g.

(3) The Characterization of Caproylated and Thiolated Multiple Modified Derivatives of Gelatin The chemical structure of caproylated and thiolated multiple modified derivatives of gelatin is as follows:

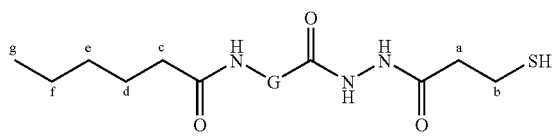

No small molecule impurity eluting peak is detected using GPC (with pure water as mobile phase, absorption detection being conducted at ultraviolet 210 nm), which indicates that the caproylated and thiolated multiple modified derivatives of gelatin is highly purified, and impurity content is below the detection level of the instrument.

Using 2,4,6-trinitrobenzenesulfonic acid (TNBS) reagent, it is measured that 33% of the side chain amino groups of gelatin are caproylated.

Measure the active thiol content of caproylated and thiolated multiple modified derivatives of gelatin using improved Ellman method published by Shu et al in Biomacromolecules, 3, 1304, 2002 and the value is 0.24 mmol thiol/g.

Detection results using $^1$H-NMR (with $D_2O$ as the solvent) are as follows:

| H | a | b | c | d | e | f | g |
|---|---|---|---|---|---|---|---|
| δ (ppm) | 2.58 | 2.72 | 2.14 | 1.45 | 1.15 | 1.15 | 0.72 |

EXAMPLE 3

Synthesis and Characterization of Butyrylated and Thiolated Multiple Modified Derivatives of Gelatin (the Multiple Modified Derivatives of Gelatin Represented by General Formula (V) of this Invention, wherein,

(1) Butyrylation of Gelatin

Dissolve 1 g gelatin (type B, made from cowskin, Sigma, America) in 100 ml distilled water (about 30° C.), and get the clear and transparent solution. Use 1.0 mol/l sodium hydroxide solution to adjust the pH value of solution to about 9.5, then add in 0.08 g butyric anhydride (analytical pure) under magnetic stirring, add in appropriate amount of 1.0 mol/l sodium hydroxide solution continuously to maintain the solution pH at alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (butyrylated gelatin) about 0.75 g.

(2) Thiolation of Butyrylated Gelatin

Take above mentioned butyrylated gelatin 0.5 g to dissolve in 50 ml distilled water (about 30° C.). Add 0.4 g disuccinicdiacylcystaminehydrazide in the above mentioned solution (prepared according to the method published in the Chinese invention patent applied by us "dihydrazide compound, preparation and usage thereof" whose application number is 200610118715.2), stir the solution. Then use 0.1 mol/l hydrochloric acid to adjust the pH value of solution to 4.75, add in 0.25 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic stirring for 2 hours, add in 2.5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.31 g.

(3) The Characterization of Butyrylated and Thiolated Multiple Modified Derivatives of Gelatin The chemical structure of butyrylated and thiolated multiple modified derivatives of gelatin is as follows:

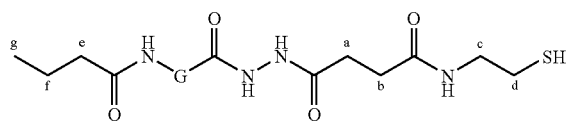

No small molecular impurity eluting peak is detected using GPC (with pure water as mobile phase, absorption detection being conducted at ultraviolet 210 nm), which indicates that the butyrylated and thiolated multiple modified derivatives of gelatin is highly purified, and impurity content is below the detection level of the instrument.

Using 2,4,6-trinitrobenzenesulfonic acid (TNBS) reagent, it is measured that 36% of the side chain amino groups of butyrylated gelatin are caproylated.

Measure the active thiol content of butyrylated and thiolated multiple modified derivatives of gelatin using improved Ellman method published by Shu et al in Biomacromolecules, 3, 1304, 2002 and the value is 0.47 mmol thiol/g.

Detection results using $^1$H-NMR (with $D_2O$ as the solvent) are as follows:

| H | a | b | c | d | e | f | g |
|---|---|---|---|---|---|---|---|
| δ (ppm) | 2.55 | 2.55 | 3.38 | 2.55 | 2.11 | 1.52 | 0.81 |

EXAMPLE 4

Synthesis and Characterization of Acetylated and Thiolated Multiple Modified Derivatives of Gelatin (the Multiple Modified Derivatives of Gelatin Represented by General Formula (V) of this Invention, wherein,

$R_2$=—$CH_3$)

(1) Acetylation of Gelatin

Dissolve 1 g gelatin (type B, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.05 g acetic anhydride (analytical pure) under magnetic stirring, add in appropriate amount of 1.0 mol/l sodium hydroxide solution continuously to maintain the pH value of solution under alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (acetylated gelatin) about 0.8 g.

(2) Thiolation of Acetylated Gelatin

Take above mentioned acetylated gelatin 0.5 g to dissolve in 50 ml distilled water (about 30° C.). Add 0.3 g dithio-dipropionodiarylglycyldihydrazide in the above mentioned solution (prepared according to the method published in the Chinese invention patent applied by us "dihydrazide compound, preparation and usage thereof" whose application number is 200610118715.2), stir the solution. Then use 0.1 mol/l hydrochloric acid to adjust the pH value of solution to 4.75, add in 0.3 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic stirring for 2 hours, add in 2.5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.3 g.

(3) The Characterization of Acetylated and Thiolated Multiple Modified Derivatives of Gelatin The chemical structure of acetylated and thiolated multiple modified derivatives of gelatin is as follows:

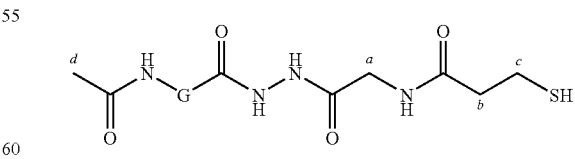

No small molecule impurity eluting peak is detected using GPC (with pure water as mobile phase, absorption detection being conducted at ultraviolet 210 nm), which indicates that the acetylated and thiolated multiple modified derivatives of gelatin is highly purified, and impurity content is below the detection level of the instrument.

Using 2,4,6-trinitrobenzenesulfonic acid (TNBS) reagent, it is measured that 52% of the side chain amino groups of acetylated gelatin are acetylated.

Measure the active thiol content of formylated and thiolated multiple modified derivatives of gelatin using improved Ellman method published by Shu et al in Biomacromolecules, 3, 1304, 2002 and the value is 0.32 mmol thiol/g.

Detection results using $^1$H-NMR (with $D_2O$ as the solvent) are as follows:

| | H | | | |
|---|---|---|---|---|
| | a | b | c | d |
| δ (ppm) | 2.57 | 3.89 | 2.68 | 1.84 |

EXAMPLE 5

Synthesis and Characterization of Succinylcarboxylated and Thiolated Multiple Modified Derivatives of Gelatin (the Multiple Modified Derivatives of Gelatin Represented by General Formula (VI) of this Invention, wherein, $R_1$=—$CH_2CH_2$—, $R_2$=—$CH_2CH_2$—, R4=—COOH)

(1) Thiolation of Gelatin

Dissolve 2 g gelatin (type B, made from cowskin, Sigma, America) in 200 ml distilled water (about 30° C.) Add 0.3 g dithio-dipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.5 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic stirring for 2 hours, add in 6 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid (thiolated gelatin) about 1.3 g.

(2) Succinylcarboxylation of Thiolated Gelatin

Take above mentioned thiolated gelatin 0.5 g under the protection of inert gas (nitrogen) to dissolve in 100 ml distilled water (about 30° C.), and get the clear and transparent solution. Use 1.0 mol/l sodium hydroxide solution to adjust the pH value of solution to about 9.0, then add in 0.05 g butanedioic anhydride (analytical pure) under magnetic stirring, add in appropriate amount of 1.0 mol/l sodium hydroxide solution continuously, maintain the pH value of solution to alkalescence (usually 8.0~9.5). Stir to react for 20 minutes about 30° C. Add 6 mol/l hydrochloric acid to adjust the pH value of the above mentioned solution to about 3.0. After that, put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid (succinylcarboxylated and thiolated multiple modified derivatives of gelatin) about 0.7 g.

(3) The Characterization of Succinylcarboxylated and Thiolated Multiple Modified Derivatives of Gelatin The chemical structure of succinylcarboxylated and thiolated multiple modified derivatives of gelatin is as follows:

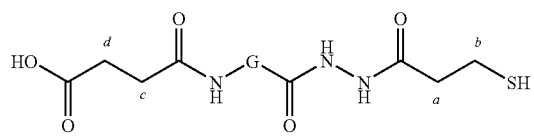

No small molecule impurity eluting peak is detected using GPC (with pure water as mobile phase, absorption detection being conducted at ultraviolet 210 nm), which indicates that the succinylcarboxylated and thiolated multiple modified derivatives of gelatin is highly purified, and impurity content is below the detection level of the instrument.

Measure the active thiol content of succinylcarboxylated and thiolated multiple modified derivatives of gelatin using improved Ellman method published by Shu et al in Biomacromolecules, 3, 1304, 2002 and the value is 0.5 mmol thiol/g.

Detection results using $^1$H-NMR (with $D_2O$ as the solvent) are as follows:

| | H | | | |
|---|---|---|---|---|
| | a | b | c | d |
| δ (ppm) | 2.56 | 2.69 | 2.45 | 2.51 |

EXAMPLE 6

Synthesis and Characterization of Succinylcarboxylated and Thiol Multiple Modified Derivatives of Gelatin (the Multiple Modified Derivatives of Gelatin Represented by General Formula (VII) of this Invention, wherein, $R_1$=—$CH_2CH_2$—, $R_3$=—$CH_2CH_2$—)

(1) Succinylcarboxylation of Gelatin

Dissolve 1 g gelatin (type B, made from cowskin, Sigma, America) in 100 ml distilled water (about 30° C.), and get the clear and transparent solution. Use 1.0 mol/l sodium hydroxide solution to adjust the pH value of solution to about 9.5, then add in 0.05 g butanedioic anhydride (analytical pure) under magnetic stirring, add in appropriate amount of 1.0 mol/l sodium hydroxide solution continuously to maintain the pH value of solution to alkalescence (usually 8.0~9.5). Stir to react for 1 hour about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (succinylcarboxylated gelatin) about 0.7 g.

(2) Thiolation of Succinylcarboxylated Gelatin

Take above mentioned succinylcarboxylated gelatin 0.5 g to dissolve in 50 ml distilled water (about 30° C.). Add 1.2 g dithiol-dipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.75 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under electromagnetic stirring for 2 hours, add in 5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.33 g.

(3) The Characterization of Succinylcarboxylated and Thiolated Multiple Modified Derivatives of Gelatin The chemical structure of succinylcarboxylated and thiolated multiple modified derivatives of gelatin is as follows:

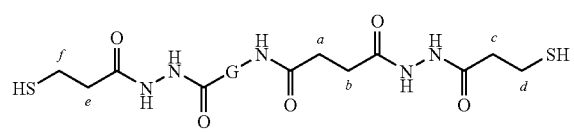

No small molecule impurity eluting peak is detected using GPC (with pure water as mobile phase, absorption detection being conducted at ultraviolet 210 nm), which indicates that the acetylated and thiolated multiple modified derivatives of gelatin is highly purified, and impurity content is below the detection level of the apparatus.

Using 2,4,6-trinitrobenzenesulfonic acid (TNBS) reagent, it is measured that 45% of the side chain amino groups of the succinylcarboxylated gelatin are succinylcarboxylated.

Measure the active thiol content of succinylcarboxylated and thiolated multiple modified derivatives of gelatin using improved Ellman method published by Shu et al in Biomacromolecules, 3, 1304, 2002. It's 0.87 mmol sulfhydryl/g.

Detection results using $^1$H-NMR (with $D_2O$ as the solvent) are as follows:

| H | a | b | c | d | e | f |
|---|---|---|---|---|---|---|
| δ (ppm) | 2.38 | 2.39 | 2.56 | 2.69 | 2.56 | 2.69 |

EXAMPLE 7

Synthesis and Characterization of Acetylated, Succinylcarboxylated and Thiolated Multiple Modified Derivatives of Gelatin (the Multiple Modified Derivatives of Gelatin Represented by General Formula (VIII) of this Invention, wherein, $R_1$=—$CH_2CH_2$—, $R_2$=—$CH_3$, $R_3$=—$CH_2CH_2$—, $R_4$=—COOH)

(1) Thiolation of Gelatin

Dissolve 2 g gelatin (type B, made from cowskin, Sigma, America) in 200 ml distilled water (about 30° C.) Add 1.2 g dithio-dipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.5 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously, and maintain the pH value of solution as 4.75. After reaction under magnetic stirring for 2 hours, add in 6 g dithiothreitol (Diagnostic Chemical Limited, America) and 0.1 mol/l sodium hydroxide solution, stir, and adjust the pH value of the solution to 8.5. After that, conduct reaction under magnetic mixing for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no micromolecular impurity eluting peak is detected using GPC (with pure water as mobile phase, absorption detection being conducted at ultraviolet 210 nm). Finally gather the solution in dialysis tube, freeze drying and get white flocculent solid (thiolated gelatin) about 1.3 g.

(2) Acetylation and Succinylcarboxylation of Thiolated Gelatin

Take above mentioned thiolated gelatin 0.5 g to dissolve in 100 ml distilled water (about 30° C.) under inert gas (nitrogen), and get the clear and transparent solution. Use 1.0 mol/l sodium hydroxide solution to adjust the pH value of solution to about 9.0, then add in 0.5 g butanedioic anhydride and 0.15 g acetic anhydride (analytical pure) under magnetic stirring, add in appropriate amount of 1.0 mol/l sodium hydroxide solution continuously, maintain the pH value of solution to alkalescence (usually 8.0~9.5). Stir to react for 20 minutes about 30° C. Add 6 mol/l hydrochloric acid to adjust the pH value of the above mentioned solution to about 3.0. After that, put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no micromolecular impurity eluting peak is detected using GPC (with pure water as mobile phase, absorption detection being conducted at ultraviolet 210 nm). Finally gather the solution in dialysis tube, freeze drying and get white flocculent solid (acetylated, succinylcarboxylated and thiolated multiple modified derivatives of gelatin) about 0.7 g.

(3) The Characterization of Acetylated, Succinylcarboxylated and Thiolated Multiple Modified Derivatives of Gelatin The chemical structure of acetylated, succinylcarboxylated and thiolated multiple modified derivatives of gelatin is as follows:

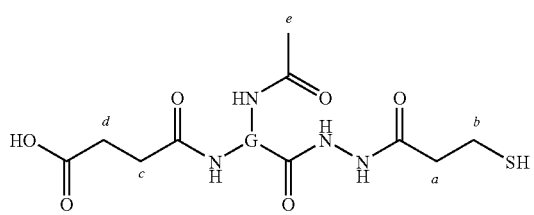

No small molecule impurity eluting peak is detected using GPC (with pure water as mobile phase, absorption detection being conducted at ultraviolet 210 nm), which indicates that the acetylated, succinylcarboxylated and thiolated multiple modified derivatives of gelatin is highly purified, and impurity content is below the detection level of the apparatus.

Measure the active thiol content of acetylated, succinylcarboxylated and thiolated multiple modified derivatives of gelatin using improved Ellman method published by Shu et al in Biomacromolecules, 3, 1304, 2002 and the value is 0.47 mmol thiol/g.

Detection results using $^1$H-NMR (with $D_2O$ as the solvent) are as follows:

| H | a | b | c | d | e |
|---|---|---|---|---|---|
| δ (ppm) | 2.56 | 2.69 | 2.45 | 2.51 | 1.83 |

EXAMPLE 8

Synthesis and Characterization of Acetylated, Succinylcarboxylated and Sulfhydrylated Multiple Modified Derivatives of Gelatin (the Multiple Modified Derivatives of Gelatin Represented by General Formula (IX) of this Invention, wherein, $R_1$=—$CH_2CH_2$—, $R_2$=—$CH_3$, $R_3$=—$CH_2CH_2$—)

(1) Acetylation of Gelatin

Dissolve 1 g gelatin (type B, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.02 g acetic anhydride (analytical pure) under magnetic stirring, add in appropriate amount of 1.0 mol/l sodium hydroxide solution continuously to maintain the pH value of solution to alkalescence (usually 8.0~9.5). Stir to react for 1 hour about 30° C. After that, put the above mentioned solution into dialysis tube (molecular weight cut off 3500, Fisher, America), dialyse the solution with distilled water, change the dialysate once per 8 hours till no micromolecular impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (acetylated gelatin) about 1.6 g.

(2) Succinylcarboxylation of Acetylated Gelatin

Take above mentioned acetylated gelatin 1 g to dissolve in 100 ml distilled water (about 30° C.), and get the clear and transparent solution. Use 1.0 mol/l sodium hydroxide solution to adjust the pH value of solution to about 9.5, then add in 0.02 g butanedioic anhydride (analytically pure) under magnetic stirring, add in appropriate amount of 1.0 mol/l sodium hydroxide solution continuously to maintain the pH value of solution to alkalescence (usually 8.0~9.5). Stir to react for 1 hour about 30° C. After that, put the above mentioned solution into dialysis tube (molecular weight cut off 3500, Fisher, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid (succinylcarboxylated and acetylated gelatin) about 0.7 g.

(3) Thiolation of Succinylcarboxylated and Acetylated Gelatin

Take above mentioned succinylcarboxylated and acetylated gelatin 0.5 g to dissolve in 50 ml distilled water (about 30° C.). Add 1.2 g dithio-dipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.75 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic mixing for 2 hours, add in 5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no micromolecular impurity eluting peak is detected using GPC (with pure water as mobile phase, absorption detection being conducted at ultraviolet 210 nm). Finally gather the solution in dialysis tube, freeze drying and get white flocculent solid about 0.33 g.

(4) The Characterization of Acetylated, Succinylcarboxylated and Thiolated Multiple Modified Derivatives of Gelatin The chemical structure of acetylated, succinylcarboxylated and thiolated multiple modified derivatives of gelatin is as follows:

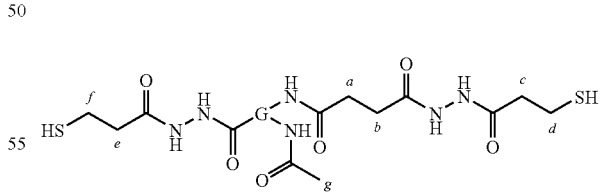

No small molecule impurity eluting peak is detected using GPC (with pure water as mobile phase, absorption detection being conducted at ultraviolet 210 nm), which indicates that the acetylated, succinylcarboxylated and thiolated multiple modified derivatives of gelatin is highly purified, and impurity content is below the detection level of the instrument.

Using 2,4,6-trinitrobenzenesulfonic acid (TNBS) reagent, it is measured that 21% of the side chain amino groups of gelatin are acetylated and 28% succinylcarboxylated.

Measure the active thiol content of acetylated, succinylcarboxylated and thiolated multiple modified derivatives of gelatin using improved Ellman method published by Shu et al in Biomacromolecules, 3, 1304, 2002 and the value is 0.64 mmol thiol/g.

Detection results using $^1$H-NMR (with $D_2O$ as the solvent) are as follows:

| H | a | b | c | d | e | f | g |
|---|---|---|---|---|---|---|---|
| δ (ppm) | 2.38 | 2.39 | 2.56 | 2.69 | 2.56 | 2.69 | 1.84 |

EXAMPLE 9

Synthesis and Characterization of Succinylcarboxylated and Thiolated Multiple Modified Derivatives of Gelatin (the Multiple Modified Derivatives of Gelatin Represented by General Formula (X) of this Invention, wherein, $R_1$=—$CH_2CH_2$—, $R_3$=—$CH_2CH_2$—)

(1) Succinylcarboxylation of Gelatin

Dissolve 1 g gelatin (type B, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.05 g butanedioic anhydride (analytically pure) under magnetic stirring, add in appropriate amount of 1.0 mol/l sodium hydroxide solution continuously to maintain the pH value of solution to alkalescence (usually 8.0~9.5). Stir to react for 1 hour about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (succinylcarboxylated gelatin) about 0.7 g.

(2) Thiolation of Succinylcarboxylated Gelatin

Take above mentioned succinylcarboxylated gelatin 0.5 g to dissolve in 50 ml distilled water (about 30° C.). Add 0.3 g dithiol-dipropionohydrazide in the above mentioned solution (prepared according to the method published by Shu et al in Biomacromolecules, 3, 1304, 2002), stir the solution. Then use 0.1 mol/l hydrochloric acid to adjust the pH value of solution to 4.75, add in 0.25 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic mixing for 2 hours, add in 2.5 g dithiothreitol (Diagnostic Chemical Limited, America) and 0.1 mol/l sodium hydroxide solution, stir, and adjust the pH value of the solution to 8.5. After that, conduct reaction under magnetic mixing for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.33 g.

(3) The Characterization of Succinylcarboxylated and Thiolated Multiple Modified Derivatives of Gelatin The chemical structure of succinylcarboxylated and thiolated multiple modified derivatives of gelatin is as follows:

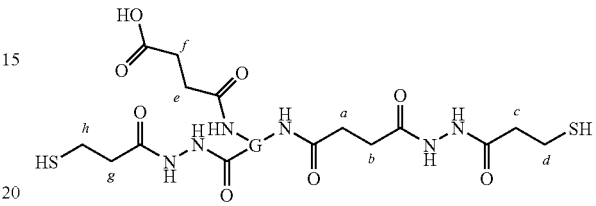

No small molecule impurity eluting peak is detected using GPC (with pure water as mobile phase, absorption detection being conducted at ultraviolet 210 nm), which indicates that the succinylcarboxylated and thiolated multiple modified derivatives of gelatin is highly purified, and impurity content is below the detection level of the apparatus.

Using 2,4,6-trinitrobenzenesulfonic acid (TNBS) reagent, it is measured that 45% side chain amino groups of gelatin were succinylcarboxylated.

Measure the active thiol content of succinylcarboxylated and thiolated multiple modified derivatives of gelatin using improved Ellman method published by Shu et al in Biomacromolecules, 3, 1304, 2002 and the value is 0.64 mmol thiol/g.

Detection results using $^1$H-NMR (with $D_2O$ as the solvent) are as follows:

| H | a | b | c | d | e | f | g | h |
|---|---|---|---|---|---|---|---|---|
| δ (ppm) | 2.38 | 2.39 | 2.56 | 2.69 | 2.45 | 2.51 | 2.56 | 2.69 |

EXAMPLE 10

Synthesis and Characterization of Succinylcarboxylated and Thiolated Multiple Modified Derivatives of Gelatin (the Multiple Modified Derivatives of Gelatin Represented by General Formula (X) of this Invention, wherein,

$R_3$=—$CH_2CH_2$—)

(1) Succinylcarboxylation of Gelatin

Dissolve 1 g gelatin (type B, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.05 g butanedioic anhydride (analytical pure) under magnetic stirring, add in appropriate amount of 1.0 mol/l sodium hydroxide solution continuously to maintain the pH value of solution to alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no micromolecular impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (succinylcarboxylated gelatin) about 0.7 g.

(2) Thiolation of Succinylcarboxylated Gelatin

Take above mentioned succinylcarboxylated gelatin 0.5 g to dissolve in 50 ml distilled water (about 30° C.). Add 0.5 g disuccinic-diarylcystaminehydrazide in the above mentioned solution (prepared according to the method published in the Chinese invention patent applied by us "dihydrazide compound, preparation and usage thereof" whose application number is 200610118715.2), stir the solution. Then use 0.1 mol/l hydrochloric acid to adjust the pH value of solution to 4.75, add in 0.25 g 1-ethyl-3-(3-dimethylamine propyl)carbodiimide hydrochloride (Aldrich, America), and conduct electromagnetic mixing. Add appropriate amount of 0.1 mol/l hydrochloric acid in the above mentioned solution continuously to maintain the pH value of solution at 4.75. After reaction under magnetic stirring for 2 hours, add in 3.0 g dithiothreitol (Diagnostic Chemical Limited, America) and 0.1 mol/l sodium hydroxide solution, stir, and adjust the pH value of the solution to 8.5. After that, conduct reaction under magnetic mixing for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mol/l hydrochloric acid solution for 3 days, change the dialysate once per 8 hours till no small molecule impurity eluting peak is detected using GPC (with pure water as mobile phase, absorption detection being conducted at ultraviolet 210 nm). Finally gather the solution in dialysis tube, freeze drying and get white flocculent solid about 0.33 g.

(3) The Characterization of Succinylcarboxylated and Thiolated Multiple Modified Derivatives of Gelatin The chemical structure of succinylcarboxylated and thiolated multiple modified derivatives of gelatin is as follows:

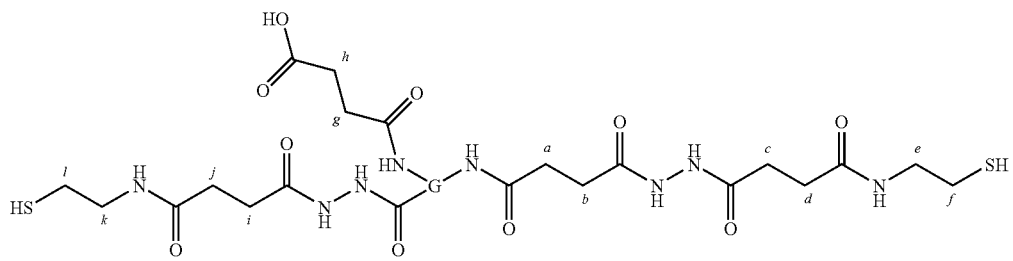

No small molecule impurity eluting peak is detected using GPC (with pure water as mobile phase, absorption detection being conducted at ultraviolet 210 nm), which indicates that the succinylcarboxylated and thiolated multiple modified derivatives of gelatin is highly purified, and impurity content is below the detection level of the instrument.

Using 2,4,6-trinitrobenzenesulfonic acid (TNBS) reagent, it is measured that 45% side chain amino groups of gelatin were succinylcarboxylated.

Measure the active thiol content of succinylcarboxylated and thiolated multiple modified derivatives of gelatin using improved Ellman method published by Shu et al in Biomacromolecules, 3, 1304, 2002 and the value is 0.611 mmol thiol/g.

Detection results using $^1$H-NMR (with D$_2$O as the solvent) are as follows:

| H | a | b | c | d | e | f | g | h | i | j | k | l |
|---|---|---|---|---|---|---|---|---|---|---|---|---|
| δ (ppm) | 2.38 | 2.38 | 2.38 | 2.38 | 2.56 | 2.69 | 2.45 | 2.51 | 2.38 | 2.38 | 2.56 | 2.69 |

EXAMPLE 11

Synthesis and Characterization of Succinylcarboxylated and Thiolated Multiple Modified Derivatives of Gelatin (the Multiple Modified Derivatives of Gelatin Represented by General Formula (XI) of this Invention, wherein, R$_1$=—CH$_2$CH$_2$—, R$_2$=—CH$_3$, R$_3$=—CH$_2$CH$_2$—)

(1) Acetylation of Gelatin

Dissolve 2 g gelatin (type B, made from pigskin, Sigma, America) in 100 ml distilled water (about 30° C.), and get the clear and transparent solution. Use 1.0 mol/l sodium hydroxide solution to adjust the pH value of solution to about 9.5, then add in 0.02 g acetic anhydride (analytical pure) under electromagnetic stirring, add in appropriate amount of 1.0 mol/l sodium hydroxide solution continuously to maintain the pH value of solution to alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (acetylated gelatin) about 1.6 g.

(2) Succinylcarboxylation of Acetylated Gelatin

Take above mentioned acetylated gelatin 1 g to dissolve in 100 ml distilled water (about 30° C.), and get the clear and transparent solution. Use 1.0 mol/l sodium hydroxide solution to adjust the pH value of solution to about 9.5, then add in 0.02 g butanedioic anhydride (analytical pure) under magnetic stirring, add in appropriate amount of 1.0 mol/l sodium hydroxide solution continuously to maintain the pH value of solution to alkalescence (usually 8.0~9.5). Stir to react for 1 hour at about 30° C. After that, put the above mentioned solution into dialysis tube (molecular weight cut off 3500, Fisher, America), dialyse the solution with distilled water, change the dialysate once per 8 hours till no small molecule impurity eluting peak is detected using gel permeation chromatography (GPC) (with pure water as mobile phase, absorption detection being conducted at ultraviolet 210 nm). Finally gather the solution in dialysis tube, freeze drying and get white flocculent solid (succinylcarboxylated and acetylated gelatin) about 0.7 g.

(3) Thiolation of Succinylcarboxylated and Acetylated Gelatin

Take above mentioned succinylcarboxylated and acetylated gelatin 0.5 g to dissolve in 50 ml distilled water (about 30° C.). Add 0.3 g dithio-dipropionohydrazide (prepared according to the method published by Shu et al in Biomacromolecules, 3, 1304, 2002), stir the solution. Then use 0.1 mol/l hydrochloric acid to adjust the pH value of solution to 4.75, add in 0.25 g 1-ethyl-3-(3-dimethylamine propyl)carbodiimide hydrochloride (Aldrich, America) with magnetic stirring. Add appropriate amount of 0.1 mol/l hydrochloric acid in the above mentioned solution continuously to maintain the pH value of solution at 4.75. After reaction under magnetic mixing for 2 hours, add in 2.5 g dithiothreitol (Diagnostic Chemical Limited, America) and 0.1 mol/l sodium hydroxide solution, stir, and adjust the pH value of the solution to 8.5. After that, conduct reaction under magnetic stirring for 24 hours at room temperature, add 6 mol/l hydrochloric acid in the above mentioned solution until the pH value of the solution is about 3.0. Put the above mentioned solution into dialysis tube (molecular weight cut off 3500, Sigma, America), dialyse the solution with 10 liters of 0.001 mol/l hydrochloric acid and 0.3 mol/l sodium chloride solution for 5 days, and change the dialysate once per 8 hours; Then dialyse the solution with 10 liters of 0.001 mmol/l hydrochloric acid solution for 3 days, change the dialysate once per 8 hours till no micromolecular impurity eluting peak is detected using GPC (with pure water as mobile phase, absorption detection being conducted at ultraviolet 210 nm). Finally gather the solution in dialysis tube, freeze drying and get white flocculent solid about 0.33 g.

(4) The Characterization of Succinylcarboxylated, Acetylated and Thiolated Multiple Modified Derivatives of Gelatin The chemical structure of succinylcarboxylated, acetylated and thiolated multiple modified derivatives of gelatin is as follows:

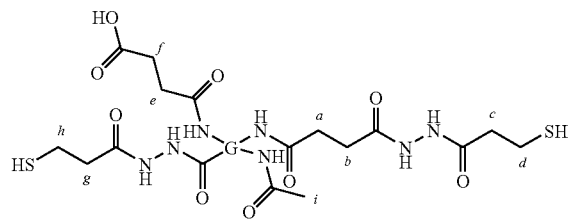

No small molecule impurity eluting peak is detected using GPC (with pure water as mobile phase, absorption detection being conducted at ultraviolet 210 nm), which indicates that the succinylcarboxylated, acetylated and thiolated multiple modified derivatives of gelatin is highly purified, and impurity content is below the detection level of the apparatus.

Using 2,4,6-trinitrobenzenesulfonic acid (TNBS) reagent, it is measured that 21% of the side chain amino groups of gelatin are acetylated and 28% succinylcarboxylated.

Measure the active thiol content of succinylcarboxylated, acetylated and thiolated multiple modified derivatives of gelatin using improved Ellman method published by Shu et al in Biomacromolecules, 3, 1304, 2002 and the value is 0.54 mmol thiol/g.

Detection results using $^1$H-NMR (with $D_2O$ as the solvent) are as follows:

| H | a | b | c | d | e | f | g | h | i |
|---|---|---|---|---|---|---|---|---|---|
| δ (ppm) | 2.38 | 2.39 | 2.56 | 2.69 | 2.45 | 2.51 | 2.56 | 2.69 | 1.84 |

EXAMPLE 12

Preparation of Crosslinked Hydrogel by Multiple Modified Derivatives of Gelatin

1. Preparation of hydrogel by PEG divinyl sulfone crosslinked with the multiple modified derivatives of gelatin of this invention: dissolve 0.3 g acetylated and thiolated multiple modified derivatives of gelatin prepared in Example 1 in 10 ml 0.1 mol/l phosphate buffer (pH=7.0) and get the clear and transparent solution. Add appropriate amount of 0.1 mol/l sodium hydroxide till the pH value is 7.4. Dissolve PEG divinyl sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG divinyl sulfone solution into 10 ml of acetylated and thiolated multiple modified derivatives of gelatin solution, conduct magnetic stirring for 30 seconds immediately, and keep standing for 30 minutes at room temperature. The solution viscosity increases gradually and forms a gel.

2. Preparation of hydrogel by PEG diacrylic ester crosslinked with the multiple modified derivatives of gelatin of this invention: dissolve 0.25 g butyrylated and thiolated multiple modified derivatives of gelatin prepared in Example 3 into 10 ml 0.1 mol/l phosphate buffer (pH=7.0) and get the clear and transparent solution. Add appropriate amount of 0.1 mol/l sodium hydroxide till the pH value is 7.4. Dissolve PEG divinyl sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG divinyl sulfone solution into 10 ml butyrylated and thiolated multiple modified derivatives of gelatin solution, conduct magnetic stirring for 30 seconds immediately, and keep standing for 30 minutes at room temperature. The solution viscosity increases gradually and forms a gel.

3. Preparation of hydrogel by PEG divinyl sulfone crosslinked with the multiple modified derivatives of gelatin of this invention: dissolve 0.2 g succinylcarboxylated and thiolated multiple modified derivatives of gelatin prepared in Example 5 into 10 ml 0.1 mol/l phosphate buffer (pH=7.0) and get the clear and transparent solution. Add appropriate amount of 0.1 mol/l sodium hydroxide till the pH value is 7.4. Dissolve PEG divinyl sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG divinyl sulfone solution into 10 ml succinylcarboxylated and thiolated multiple modified derivatives of gelatin solution, conduct magnetic stirring for 30 seconds immediately, and keep standing for 30 minutes at room temperature. The solution viscosity increases gradually and forms a gel.

4. Preparation of hydrogel by PEG divinyl sulfone crosslinked with the multiple modified derivatives of gelatin of this invention: dissolve 0.3 g succinylcarboxylated and thiolated multiple modified derivatives of gelatin prepared in Example 6 into 10 ml 0.1 mol/l phosphate buffer (pH=7.0) and get the clear and transparent solution. Add appropriate amount of 0.1 mol/l sodium hydroxide till the pH value is 7.4. Dissolve PEG divinyl sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG divinyl sulfone solution into 10 ml succinylcarboxylated and thiolated multiple modified derivatives of gelatin solution, conduct magnetic stirring for 30 seconds immediately, and keep standing for 30 minutes at room temperature. The solution viscosity increases gradually and forms a gel.

5. Preparation of hydrogel by PEG divinyl sulfone crosslinked with the multiple modified derivatives of gelatin of this invention: dissolve 0.3 g acetylated, succinylcarboxylated and thiolated multiple modified derivatives of gelatin prepared in Example 8 into 10 ml 0.1 mol/l phosphate buffer (pH=7.0) and get the clear and transparent solution. Add appropriate amount of 0.1 mol/l sodium hydroxide till the pH value is 7.4. Dissolve PEG divinyl sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG divinyl sulfone solution into 10 ml succinylcarboxylated and thiolated multiple modified derivatives of gelatin solution, conduct magnetic stirring for 30 seconds immediately, and keep standing for 30 minutes at room temperature. The solution viscosity increases gradually and forms a gel.

6. Preparation of hydrogel by PEG divinyl sulfone crosslinked with the multiple modified derivatives of gelatin of this invention: dissolve 0.3 g succinylcarboxylated and thiolated multiple modified derivatives of gelatin prepared in Example 9 into 10 ml 0.1 mol/l phosphate buffer (pH=7.0) and get the clear and transparent solution. Add appropriate amount of 0.1 mol/l sodium hydroxide till the pH value is 7.4. Dissolve PEG diethylene sulfone (molecular weight of 3400, Nektar Therapeutics, America) 0.1 g into 2.5 ml 0.1 mol/l phosphate buffer (pH=7.0) and get the clear and transparent solution. Then add the above mentioned 2.5 ml PEG diethylene sulfone solution into 10 ml the solution of acetylated and sulfydrylated multiple modified derivatives of gelatin, conduct electromagnetic stirring for 30 seconds immediately, and keep standing for 30 minutes at room temperature. The solution viscosity increases gradually and gelates.

7. Preparation of hydrogel by PEG divinyl sulfone and PEG diacrylic ester crosslinked with the multiple modified derivatives of gelatin of this invention: dissolve 0.15 g acetylated and thiolated multiple modified derivatives of gelatin prepared in Example 1 and 0.15 g succinylcarboxylated and thiolated multiple modified derivatives of gelatin prepared in Example 9 into 10 ml 0.1 mol/l phosphate buffer (pH=7.0) and get the clear and transparent solution. Add appropriate amount of 0.1 mol/l sodium hydroxide into the above mentioned solution till the pH value is 7.4. Dissolve PEG divinyl sulfone (molecular weight of 3400, Nektar Therapeutics, America) 0.05 g and PEG diacrylic ester (molecular weight of 3400, Nektar Therapeutics, America) 0.05 g simultaneously into 2.5 ml 0.1 mol/l phosphate buffer (pH=7.0) and get the clear and transparent solution. Then add the above mentioned 2.5 ml PEG divinyl sulfone/PEG diacrylic ester mixture solution into 10 ml acetylated and thiolated multiple modified derivatives of gelatin solution, conduct magnetic stirring for 30 seconds immediately, and keep standing for 30 minutes at room temperature. The solution viscosity increases gradually and forms a gel.

EXAMPLE 13

Crosslinked Hydrogel of Multiple Modified Derivatives of Gelatin as the Matrix for Cell Adhesion and Growth Prepare 6 kinds of crosslinked hydrogel of multiple modified derivatives of gelatin in 24-cell standard culture plate according to Example 12, with 0.4 ml for each cell. After 12 hours, the whole culture plate is immersed in 75% alcoholic solution for sterilization for 2 hours. After that, immerge and wash the culture plate for 3 times using sterile physiological saline solution. Add 1 ml cell culture fluid (DMEM, 10% bovine serum) and 20 thousands of NIH 3T3 fibroblasts for each cell. Culture the cells in a cell incubator with carbon dioxide circumstance for 24 hours at 37° C. Through microscope, it was observed that adhesion and spreading of cells in the surface of crosslinked hydrogel of multiple modified derivatives of gelatin are similar to that in blank culture plate, with cells assuming fusiform, which indicates that the crosslinked hydrogel of multiple modified derivatives of gelatin is an excellent matrix for cell adhesion and growth.

Industrial Practicability

The multiple modified derivatives of gelatin published in this invention have flexible chemical structure and many properties. For the multiple modified derivatives of gelatin represented by general formulas (V), (VIII), (IX) and (XI) of this invention, modification on the side chain amino group of gelatin and introduction of hydrophobic group improve the hydrophobic property of the multiple modified derivatives of gelatin of this invention, change the properties of aqueous solution, promote the formation of hydrophobic micelle and improve the solublization for hydrophobic substances (e.g. drugs etc). Meanwhile, thiolation on side chain carboxyl of gelatin provides active thiol which can be used as the active site with high reactivity for further chemical modification (e.g. preparing crosslinked material with the highly biocompatible crosslinkers etc.). For the multiple modified derivatives of gelatin represented by general formulas (VI), (VII), (VIII), (IX), (X) and (XI) of this invention, modification on the side chain amino group of gelatin introduces additional carboxyl, which alters the properties of aqueous solution and improves the hydrophilic property of the multiple modified derivatives of gelatin of the invention. Meanwhile, it is more important that transformation of amino group into carboxyl greatly improves the content of carboxyl which can be used for further chemical modification (for example, the content of side chain carboxyl of type B gelatin can be increased by as much as 24%, while that of type A can be increased by as much as 50%). In addition, these carboxyls and those that gelatin originally can be conducted with thiolation, and provide active thiol which can be used as the active site with high reactivity for further chemical modification (e.g. preparing crosslinked material with the highly biocompatible crosslinkers etc.).

The crosslinked materials with high biocompatible can be prepared conveniently by this invention, and they can be formulated into various forms e.g. thin film, sponge, gel etc, and can be used as the matrix for cell growth and so on.

The invention claimed is:

1. A modified gelatin, comprising the structure of formula (I) and at least one of the structures of formula (II), (III), and (IV) as well:

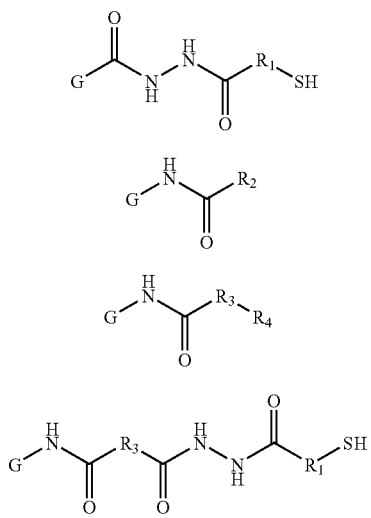

wherein,
G refers to a gelatin residue, which is a type A gelatin, a type B gelatin or a gelatin obtained from gene recombination;
$R_1$ refers to alkylene, or a linkage group with amide;
$R_2$ refers to alkyl, or aryl;
$R_3$ refers to alkylene; and
$R_4$ refers to carboxyl or carboxylate.

2. The modified gelatin according to claim 1, wherein $R_1$ and $R_3$ refer to alkylene, $R_2$ refers to alkyl, $R_4$ refers to carboxyl, carboxylate with sodium or carboxylate with potassium salt.

3. The modified gelatin according to claim 2, wherein $R_1$ and $R_3$ refer to an alkylene with 1~15 carbon atoms.

4. One or more crosslinked materials made of the modified gelatin according to claim 3 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

5. The modified gelatin according to claim 2, wherein $R_2$ refers to an alkyl with 1~15 carbon atoms.

6. One or more crosslinked materials made of the modified gelatin according to claim 5 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

7. One or more crosslinked materials made of the modified gelatin according to claim 2 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

8. The modified gelatin according to claim 1, wherein $R_1$ refers to a linkage group with amide, $R_3$ refers to alkylene and $R_2$ refers to alkyl.

9. The modified gelatin according to claim 8, wherein said linkage group with amide refers to

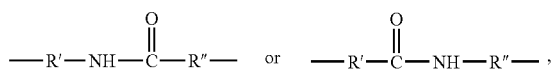

wherein R' and R" independently refer to alkylene, substituted alkylene, aryl or polyether group.

10. One or more crosslinked materials made of the modified gelatin according to claim 8 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

11. The modified of gelatin according to claim 1, wherein $R_1$ refers to a linkage group with amide, $R_3$ refers to an alkylene with 1~15 carbon atoms and $R_2$ refers to an alkyl with 1~15 carbon atoms.

12. The modified gelatin according to claim 11, wherein said linkage group with amide refers to

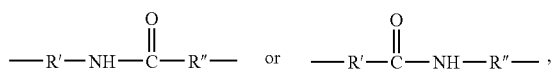

wherein R' and R" independently refer to alkylene, substituted alkylene, aryl or polyether group.

13. One or more crosslinked materials made of the modified gelatin according to claim 11 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

14. The modified gelatin according to claim 1, wherein said linkage group with amide refers to

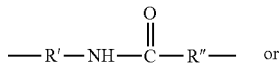

wherein R' and R" independently refer to alkylene, substituted alkylene, aryl or polyether group.

15. One or more crosslinked materials made of the modified gelatin according to claim 14 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

16. One or more crosslinked materials made of the modified gelatin according to claim 1 crosslinked by two-arm, three-arm or multi-arm polyethylene glycol (PEG) derivatives with at least two of the same or different thiol-reactive functional groups, wherein the molecular weight of said PEG derivatives is from 100 to 1000000.

17. The crosslinked material according to claim 16, wherein said thiol-reactive functional groups are selected from the group consisting of maleimide, vinyl sulfone, α,β-unsaturated acrylic ester, α,β-unsaturated methyl acrylic ester, iodo-propionic ester, bromo-propionic ester, iodo-propionamide, bromo-propionamide, disulfo-pyridine, and N-hydroxyl succimide activated ester.

* * * * *